United States Patent [19]

Bernoco et al.

[11] 4,148,607
[45] Apr. 10, 1979

[54] APPARATUS AND ANALYSIS FOR AGGLUTINATION REACTION

[75] Inventors: Domenico Bernoco, Rheinfelden; André Mottu, Basel; Lothar Waltz, Ettingen, all of Switzerland

[73] Assignee: Hoffmann-La Roche Inc., Nutley, N.J.

[21] Appl. No.: 658,204

[22] Filed: Feb. 17, 1976

[30] Foreign Application Priority Data

Feb. 28, 1975 [CH] Switzerland .................. 2567/75

[51] Int. Cl.² ............ G01N 33/16; G01N 21/60; G01N 31/02; G01N 31/14
[52] U.S. Cl. .................... 23/230 B; 23/230.3; 195/103.5 R; 233/1 R; 356/39; 356/427; 424/1; 424/11; 422/72; 422/79
[58] Field of Search ............ 23/259, 253 R, 230 B; 424/11; 195/103.5 R; 356/197

[56] References Cited

U.S. PATENT DOCUMENTS

| | | | |
|---|---|---|---|
| 3,488,156 | 1/1970 | Good | 23/259 |
| 3,586,484 | 6/1971 | Anderson | 23/230 R |
| 3,677,710 | 7/1972 | Hirsch | 424/11 X |
| 3,759,666 | 9/1973 | Hill | 23/253 R X |
| 3,770,380 | 9/1973 | Smith | 23/230 B |
| 3,838,809 | 10/1974 | Williams | 23/259 X |
| 3,841,838 | 10/1974 | Natelson | 23/259 |
| 3,883,308 | 5/1975 | Matte | 23/259 |
| 3,899,296 | 8/1975 | Mailen | 23/259 |
| 3,970,427 | 7/1976 | Esposito | 23/230 B |

FOREIGN PATENT DOCUMENTS

| | | |
|---|---|---|
| 1185228 | 3/1970 | United Kingdom. |
| 1212414 | 11/1970 | United Kingdom. |
| 1337425 | 11/1973 | United Kingdom. |
| 1378406 | 12/1974 | United Kingdom. |

OTHER PUBLICATIONS

"Gradwohl's Clinical Laboratory Methods", S. Frankel, ed., vol. 1, 7th Edition, 756-757, C. V. Mosby, St. Louis, 1970.

Primary Examiner—Sidney Marantz
Attorney, Agent, or Firm—Jon S. Saxe; Bernard S. Leon; Mark L. Hopkins

[57] ABSTRACT

Analysis of and apparatus for studying simple or complex agglutination reactions, such as for blood analysis and in particular blood groupings in which the specimen is mixed with at least one reagent in a vessel of predetermined shape and this mixture is incubated and thereafter centrifuged in this vessel. The nature of the reaction, the operations performed on the mixture and the shape of the vessel are such as to provide at cessation of the centrifuging the accumulation of the agglutinated particles at a particular location in the vessel. Following a waiting period in which the mixture is given the opportunity to partly or substantially entirely move under the influence of gravity away from said location, the path of said movement is observed by an optical arrangement which enables determination of the nature of the reaction, i.e. the presence or absence of agglutinated or non-agglutinated elements is observed after a time interval sufficient to permit their separation.

27 Claims, 25 Drawing Figures

APPARATUS AND ANALYSIS FOR AGGLUTINATION REACTION

BACKGROUND OF THE INVENTION

The invention relates to a novel analysis process based on a simple or complex agglutination reaction, inter alia for blood analysis, more particularly but not exclusively for blood groupings, and to a novel apparatus for carrying the process into practice.

The known methods, most of which are either manual or part-automatic, use vessels (cavities) in which the reactions proceed. The vessels are either individual or grouped on a flat support. They are usually made of glass or plastics.

The vessels are usually of cylindrical shape and have either conical or spherical ends; they are of course open at the top so that they may be filled. Also, so that vessels grouped on a plate may be produced, the vessel axes must be parallel to one another.

In the case of grouped vessels, the same are disposed in rows in a perpendicular arrangement - i.e., they ae distributed in a rectangular or square shape on their support.

In endeavors to save on reagents, which are often costly, the tendency is to reduce vessel dimensions and therefore the dimensions of the support plates.

However, when a large number of vessels, even small vessels, are arranged on a support, it is impossible to arrange for centrifuging such that the axis of each vessel is completely coaxial with the direction of the centrifuging force, since the vessels are disposed in parallel relationship to one another. The only way of complying with such a condition is for the centrifuge to be of infinite radius. Consequently, agglutination after centrifuging for any given kind of reaction is not the same for each vessel. Some of the globules remain free in some vessels since such globules have been displaced on to the cone surface, and not its apex, by the centrifugal force.

As a check on the nature and quality of the reaction, the globules must be returned to the suspended state after centrifuging, to which end the plate is given a vibratory treatment for varying lengths of time. Interpretation of results is baaed on observation and estimation of the relative quantities of globules which have agglutinated and of globules which have remained in suspension. The estimation is made all the more difficult in that, when a large number of vessels are disposed on a support, the phenomenon of agglutination during centrifuging may be different in all of the vessels on the plate, for the reasons just mentioned.

SUMMARY OF THE INVENTION

This invention provides an analysis process and an apparatus for carrying the process into practice such that the difficulties mentioned are obviated because the direction of the centrifugal force is completely coaxial with the axis of each vessel. Also, the process and apparatus according to the invention make possible automatic reading of results which makes for reliable interpretation, based on very small amounts of specimen and reagents.

In the novel process which may involve simple or complex agglutination reactions, (a) a specimen for analysis is mixed with one or more reagents in a vessel of progressively decreasing cross-section; (b) the mixture is incubated; (c) the incubated mixture is then centrifuged at least one so as to hurl the particles onto the vessel base, the same being disposed substantially in the direction of the centrifugal force, with the result that the agglutinated particles stick to the vessel base whereas the unagglutinated elements remain free thereon, whereafter (d) centrifuging is stopped and, if necessary, operations (a), (b), (c) and (d) are repeated on the resulting product and a different reagent and the nature of the reaction which has occurred is determined by observing the presence or absence of the agglutinated or non-agglutinated elements, after a time interval sufficient for their separation.

The process can be carried into practice very advantageously with the use of a novel apparatus developed for the purpose.

BRIEF DESCRIPTION OF THE DRAWINGS

A detailed description will now be given of the process and apparatus with reference to the accompanying drawings, in which.

DESCRIPTION OF THE PREFERRED EMBODIMENT(S)

The main use for the purpose is in blood analysis. In blood analysis it is usually preferred to separate the blood specimen to be analyzed into globules and plasma before the process is carried into effect. Conveniently, the separation can be carried out by centrifuging, e.g. using a commercially available centrifuge.

It has also been found advantageous if, before being placed in the vessel in which the mixing step (a) is performed, the blood specimen has added to it an enzyme, such as bromelin, accelerating the agglutination or clumping reaction.

Since the volume of the blood specimen is very reduced, being e.g. 5 μl per vessel, it has been found that the vessel walls have appreciable hydrophilic or hydrophobic effects. It is therefore advisable to cover the vessel walls before use with a thin layer of proteins to ensure that the mixing step (a) is performed correctly. There can be used for this purpose e.g. ox-blood serum albumins. For the rest, the protein coating can be given, as required, to either the entire wall surface or just to some of the wall surface, and the proteins used can be all of the same or of various kinds. The use of various kinds of protein instead of or concurrently with the variant of partial coating can be considered when different hydrophilic or hydrophobic effects are required on different portions of the vessel walls.

The steps hereinbefore described, although useful for the practice of the process, are optional. Consequently, either after one or the other of the steps just outlined or directly, the blood specimen to be analyzed is prepared (by dilution). One possible practical procedure is the following:

One or more dilution tubes or "hoods" is or are added to the specimen tube and they are introduced into a conveyor system which can be a chain system or a rotating system or any other appropriate system. The conveyor moves each system embodied by a specimen tube and a hood past one or more dilution stations. The same preferably comprise a probe, the same sampling the red globules in the specimen tube, and an element for transferring the red globules into the or each hood associated with the specimen tube. Simultaneously with probe movement, one or more pumps deliver or delivers to the or each hood a physiological solution which may or may not contain an enzyme such as bromelin. The time taken to prepare and to dilute the specimen in this way is approximately twelve minutes.

It is is required to use the apparatus for blood groupings by the bromelin method and by the Coombs method simultaneously, two hoods are required, one containing the physiological solution and the bromelin, while the other contains only the physiological solution.

The process can then be carried into effect, preferably by means of the apparatus to be described in greater detail hereinafter. Basically, such apparatus comprises a number of vessels 1 (e.g. FIG. 1) secured to a support 2. Preferably, the support resembles in shape a ring or a disc. Each vessel 1 is formed with a top aperture 3 for the introduction of the specimen for analysis and of the reagents, each vessel having a place or site 4 for receiving the specimen and reagents. In the embodiment shown for example in FIG. 1, the site 4 takes the form of a recess or hollow of a kind such that the specimen and reagents collect therein, provided that they are subject only to the force of gravity.

Figures 12, 13:
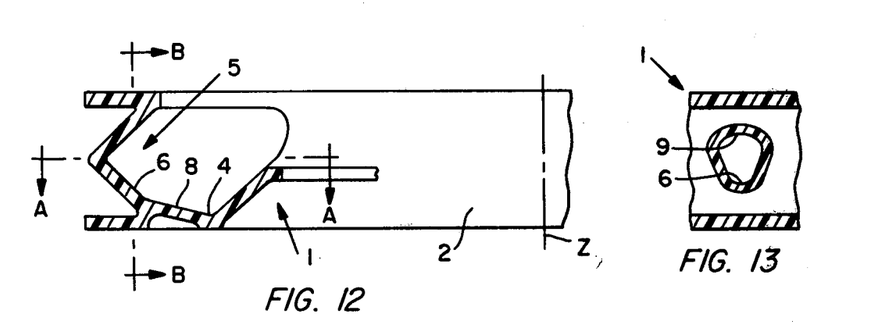
FIG. 12 shows the constructional arrangement of the shape of the vessel.
FIG. 13 is a section on the line B—B of FIG. 12.
Figure 14:
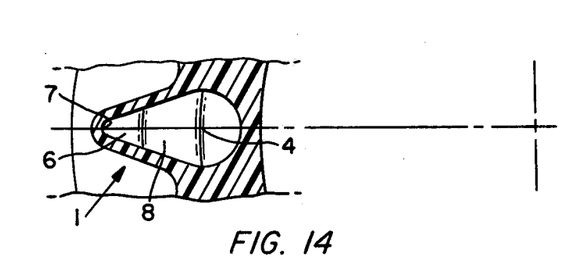
FIG. 14 is a section on the line A—A of FIG. 12.

As can be seen in FIGS. 12 to 14, the vessel cross-section decreases continuously towards the outside in its terminal portion 5 — i.e., the portion remote from the centrifuging axis Z. Also, in that part of the site 4 which is remote from the centrifuging axis Z, the vessel has a surface 6 which inclines upwardly towards the outside as far as a location 7 of the terminal portion of the vessel where the cross-section thereof is at the narrowest dimension.

The vessels are filled with the red globule specimens of the blood to be analyzed and the test sera and with the specimens of the corresponding plasma and the test globules. In routine blood grouping, there may be the following distribution of specimens and reagents relatively to one another:

| Vessel | specimen | reagent |
|---|---|---|
| 1 | reference substance | (for color intensity) |
| 2 | red globules | anti serum A |
| 3 | red globules | anti serum B |
| 4 | red globules | anti serum A+B |
| 5 | plasma | globules $A_1$ |
| 6 | " | globules $A_2$ |
| 7 | " | globules B |
| 8 | " | globules 0 | to which are usually added in case of determination of the rhesus factor

| | | |
|---|---|---|
| 9 | red globules | anti serum D no. 1 (or anti D) |
| 10 | red globules | anti serum D no. 2 (or anti CDE) |

Also, and either concurrently with the determinations just described or in a subsequent step, the determination (on the red globules) of antigens other than A and B, e.g. Kell's antigen, or of sub-groups of A or of AB and, on the plasma, of abnormal agglutinimes and of syphilis can be arranged for. The control to which the sensitivity of the reading device is adjusted can be inter alia a suspension of globulin or a suspension of red globules in albumin.

Step (a) of mixing the specimens for analysis with the reagents can be carried out quite simply by vibrating the vessel horizontally or vertically or both simultaneously before and/or during the incubation step (b) and on a periodic or continuous basis. Mixing occurs in that part of the vessel which has the reference 4 in FIG. 1 (See e.g. FIG. 2).

The reaction takes some time to develop its full effect. The mixture must therefore be left for a sufficiently long incubation time (b); if required, incubation can be speeded up or completed by the vessel being vibrated as hereinbefore described.

Figure 3:
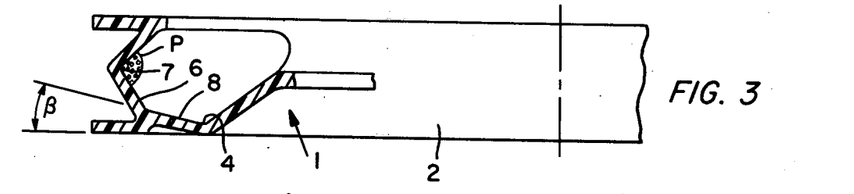
FIG. 3 shows the same vessel after centrifuging.
Figure 4:
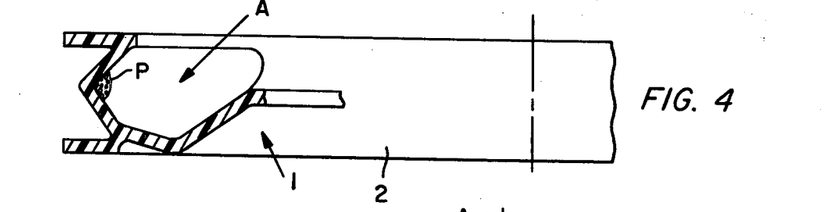
FIG. 4 shows the vessel during reading of the reaction, the arrow A representing the direction of a light beam passing through the vessel.
Figure 5A:
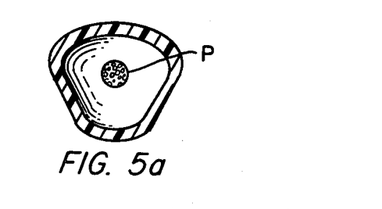
FIGS. 5a and 5b represent the image of a positive reaction.
Figure 5B:
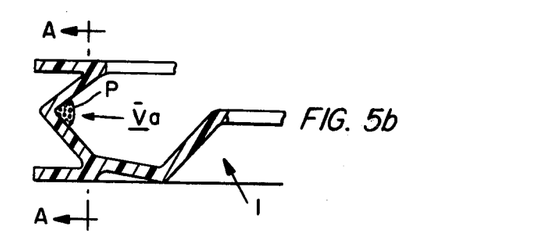
Figure 6A:
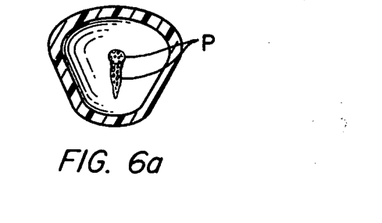
FIGS. 6a and 6b represent the image of a negative reaction.
Figure 6B:
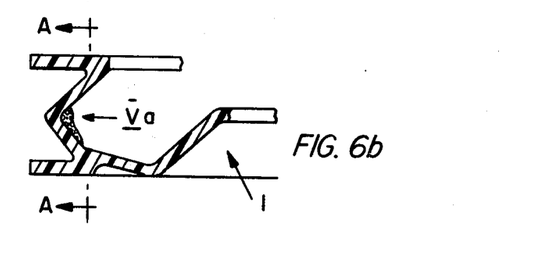
Figure 7:
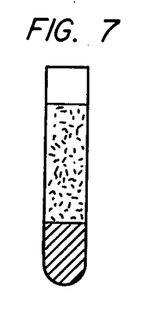
FIG. 7 shows how the red globules and the plasma are separated in blood analysis.
Figure 8:
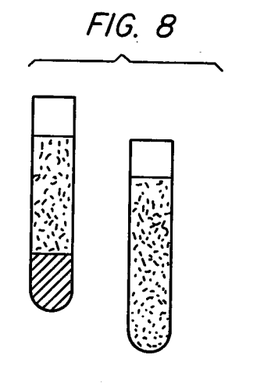
FIG. 8 shows treatment of the blood specimen by an enzyme accelerating the agglutination or clumping reaction.

The incubated mixture is then given the centrifuging step (c) so that the mixture is hurled against the vessel base 7 (FIG. 3). Centrifuging is by rotation of the vessel around the axis Z along which it is secured and it can be repeated or given in consecutive steps at various speeds.

Figure 1:
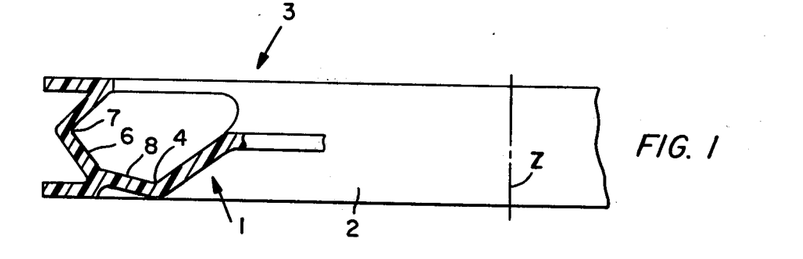
FIG. 1 is a section through a support in which a vessel is received.
Figure 2:
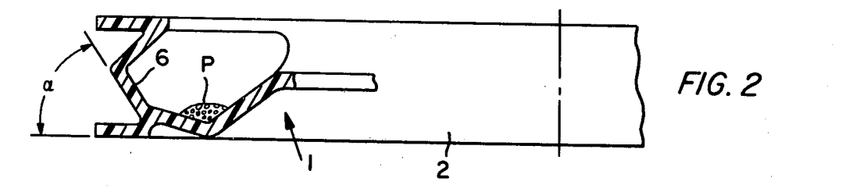
FIG. 2 shows the vessel of FIG. 1 after charging.

Upon the cessation of centrifuging (step [d]), for example after a few minutes, one of the two following cases may be observed:

I. If the reaction is positive, agglutination is complete and the agglutinates remain stuck to the vessel base portion 7;

II. If the reaction is completely or partly negative, the non-agglutinated elements, e.g. the non-agglutinated red globules, slide down from the vessel base 7 along the inclined wall 6 (FIG. 1).

The slide-down does not start immediately upon the cessation of centrifuging but usually starts after a short wait. Also, the rate of sliding may vary according to the nature and intensity of the reaction occurring, and so measurement of the rate of sliding gives further information on the extent of negative reactions.

Reading of the reaction (FIG. 9) — i.e., observation of the presence or absence of unagglutinated elements on the inclined wall — can be accomplished for example by means of a visual microscope arrangement. Preferably, however, reading is automatic and can be provided for example by a facility comprising inter alia a microscope and a photoelectric cell. The microscope can also have one or more filters making it possible to read the result of the reaction at various wavelengths. The reaction can also be read by measuring the varying extents of transparency of the agglutinated elements remaining on the vessel base after a particular time. If the specimen or the reagent used is radioactive or contains a radioactive addition substance, the nature of the reaction is determined automatically by means of a facility comprising a radioactivity counter.

The process is also of use for blood groupings by the Coombs' test or method. In this event the product arising after step (d) (cessation of centrifuging) is treated by further steps for facilitating agglutination, including washing and returning the reaction product to the suspended state. For washing, an appropriate washing liquid, such as a physiological solution or an anti-globulin solution, in a predetermined quantity and directed towards the vessel base can be used, the stream being produced by pressure injection. The vessel can also be vibrated vigorously horizontally and/or vertically.

After these further steps, the cycle of step (a), (b) (c) and (d) is repeated on the washed and re-suspended product, to which a new reagent has been added, and the resulting reaction is read in the manner hereinbefore described.

An embodiment of the apparatus for carrying the process into effect will now be described.

As previously described, the supports have a number of vessels or receptacles or the like 1 formed with an aperture 3, a place or site 4 for receiving the specimen and reagents, and an inclined surface 6.

Surface 6 is at an angle $\alpha$ to the horizontal, such angle being between 30° and 60°. In a special variant the angle is from 45° to 50°. The optimum angle depends, of course, upon the particular reagents used, the centrifuging speed and the nature of the specimens for analysis. The base of the inclined surface 6 can be plane but is preferably concave.

Figure 15:
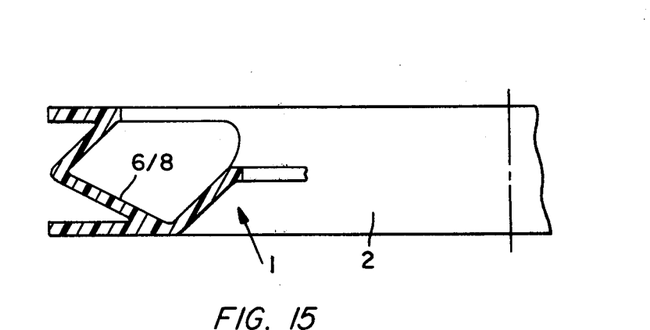
FIG. 15 shows an alternative shape for the vessel.

Referring to FIG. 3, between the location 4 and the surface 6 there is an intermediate or transition zone 8 which is inclined but which could be horizontal, the inclination angle $\beta$ of zone 8 is, in FIG. 3, a fraction of the inclination angle $\alpha$ (FIG. 2) of surface 6. Satisfactory results were obtained with an angle $\beta$ of from 8° to 20°, but the value can be higher. FIG. 15 shows a variant in which the angle $\beta$ of the zone 8 coincides with the angle of the surface 6.

As shown in FIGS. 12 to 14, the terminal cross-section 5 of vessel 1 is bounded by the surface 6 at the bottom and by a tunnel-shaped passage at the top. The section A—A in FIG. 14 shows the progressively decreasing cross-section of the vessel, such cross-section reaching its lowest value at the location 7.

Figure 9:
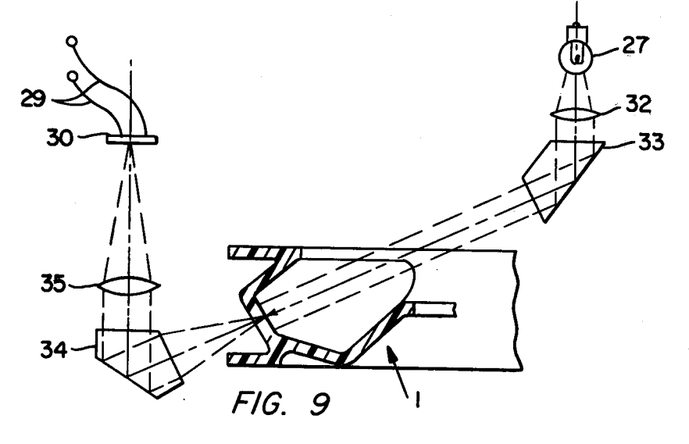
FIG. 9 shows a photoelectric measuring device for analyzing the results.
Figure 10:
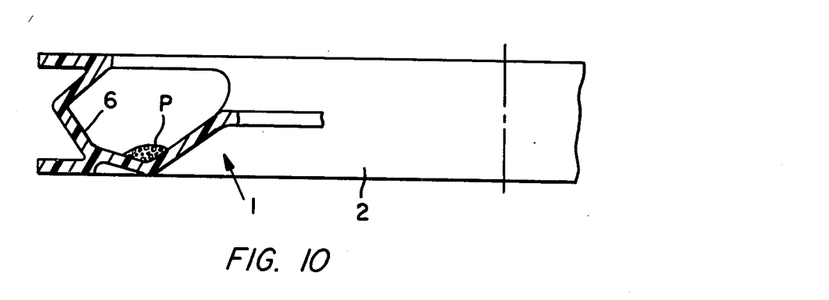
FIG. 10 is diagrammatic view of a vessel during vibration of the mixture.
Figure 11:
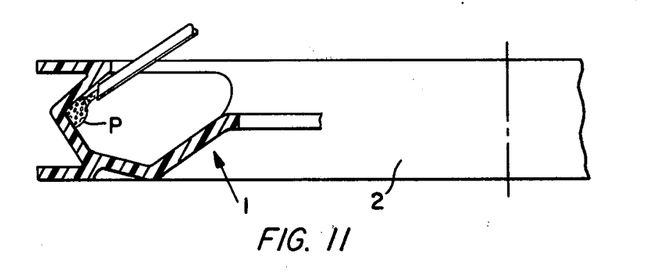
FIG. 11 shows the vessel of FIG. 10 during the resuspension step by a stream.

Since there are advantages in using a photoelectric system to study the reaction, the vessel is embodied, at least in the part near the inclined surface 6, by a transparent substance, preferably plastics (see e.g. FIG. 9).

Figure 16:
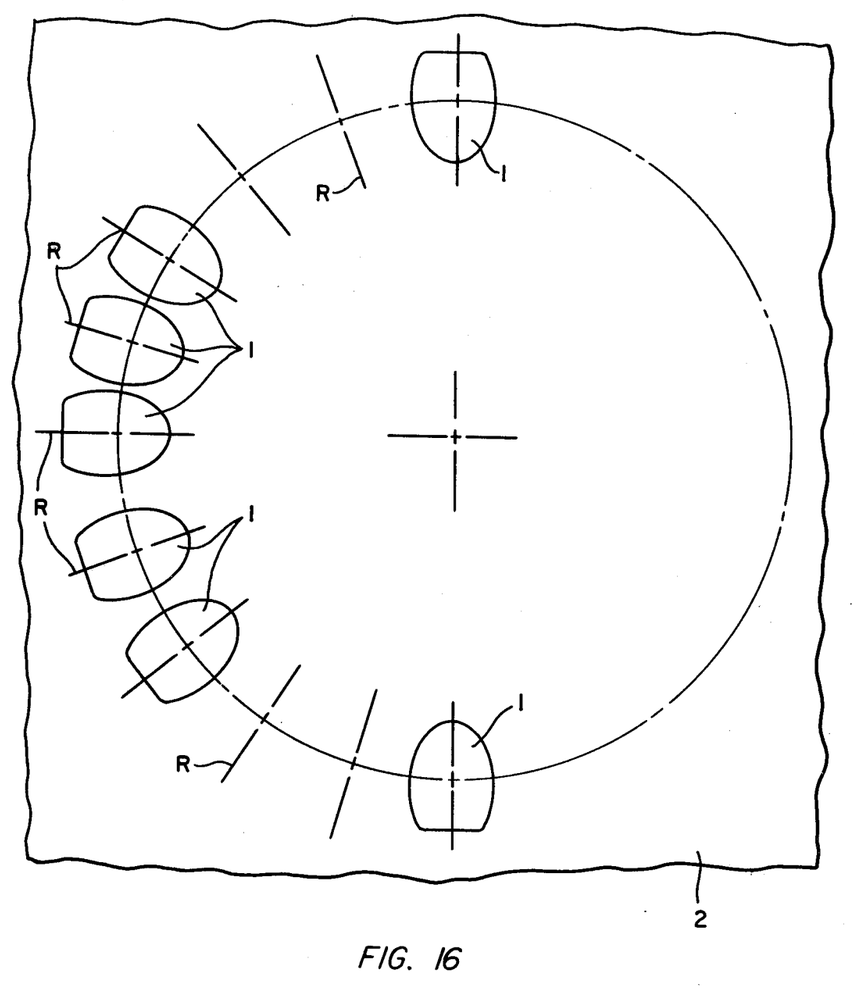
FIG. 16 is a view showing the arrangement of a number of vessels on a support.

To facilitate the performance of the process according to the invention, a number of vessels 1 are arranged in the shape of an open or closed circle on the support 2 (e.g. FIG. 17), the main axes of the vessels being disposed along radii$^R$ which all converge towards the axis Z (e.g. FIG. 12 or 16) of the support 2. Consequently, all the vessels are at the same distance from the axis Z. However, a number of concentric rows of vessels 1 could be placed on a single support 2.

Figure 17:
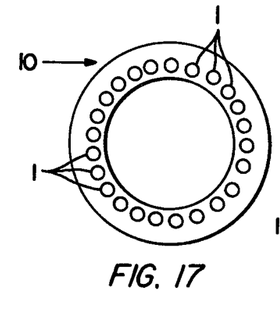
FIGS. 17 to 21 show alternative shapes for the support.

Of the many possible ways of distributing the vessels 1 on a support, those shown in FIGS. 17 to 21 have been selected. Referring to FIG. 17, the vessels 1 are arranged on a support 10 in the shape of a closed circle. However, it may be advantageous if there is an aperture 12 in a substantially circular support 11, in the manner shown in FIG. 18, so that the support 11 can be slid laterally around a spindle or placed on an appropriately shaped arm.

Figure 19:
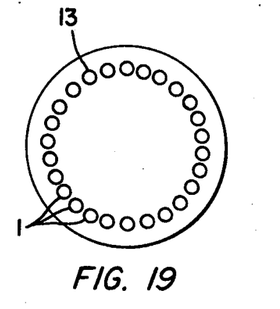
Figure 20:
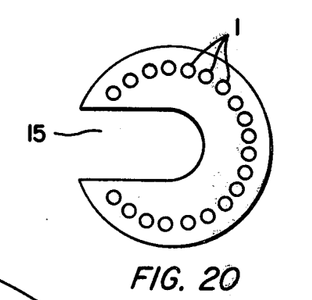

The support 13 shown in FIG. 19 can take the form of a closed disc which, as shown in FIG. 20, can also be formed with a recess 15.

Figure 21:
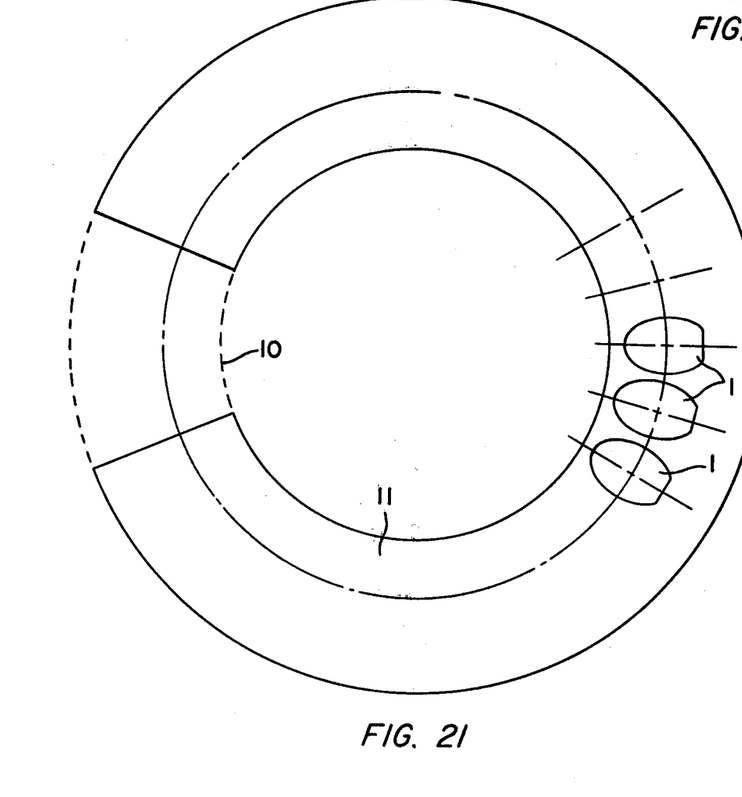

FIG. 21 is a view to an enlarged scale showing vessels 1 arranged in an open circle 10 and a closed circle 11.

Measurement of whether the reactions are positive or negative, in accordance with FIGS. 5a–5b and 6a–6b, are made in satisfactory conditions by means of a photoelectric facility diagrammatically shown in FIG. 9. A light beam from a light source 27 is made parallel by a condenser 32, passes through prisms 33, 34 and goes through a final lens 35 to reach cell 30; the same has wires 29 connected to an electrical measuring instrument (not shown).

Figure 22:
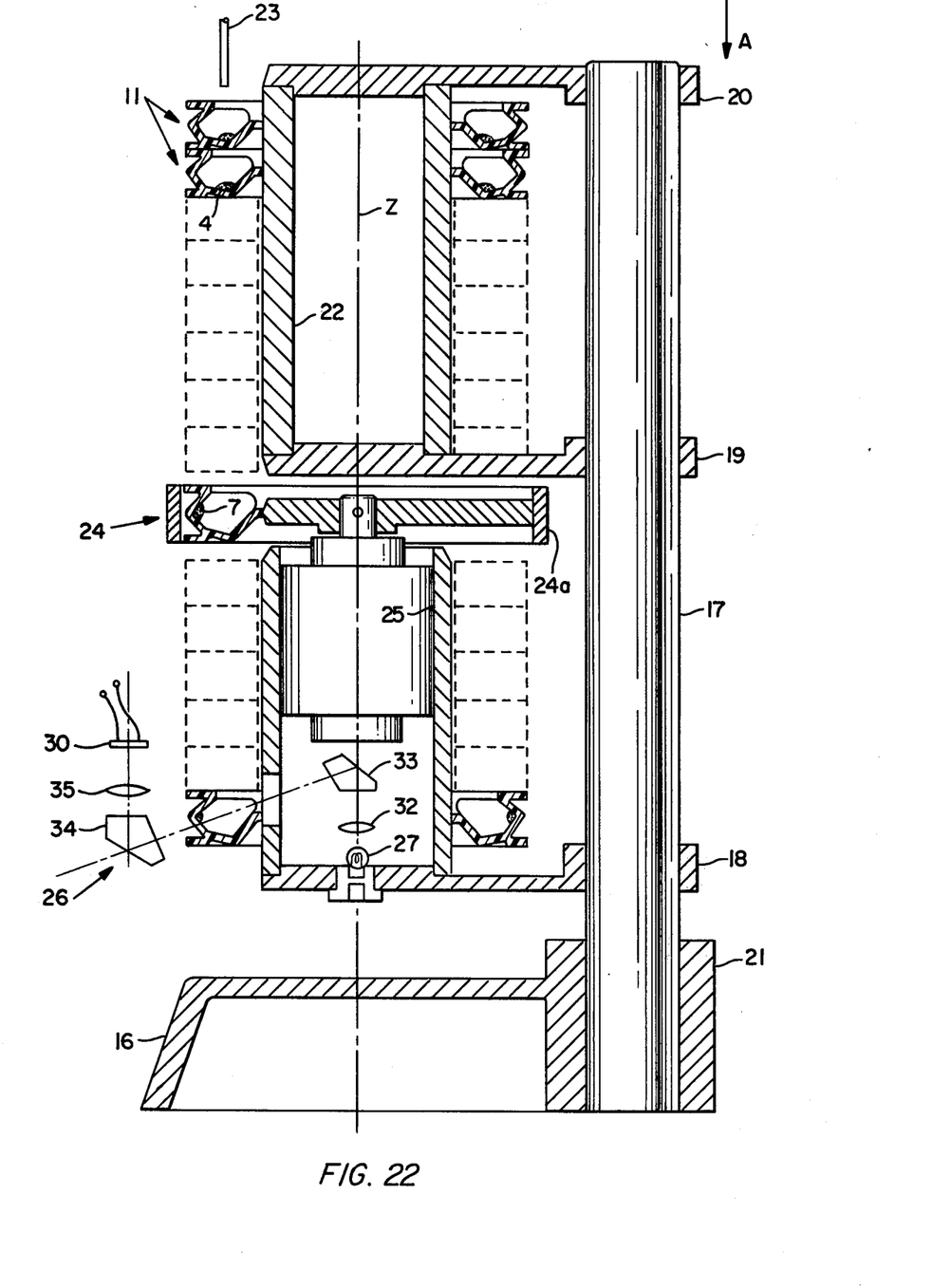
FIG. 22 is a simplified section through an automatic apparatus for performing the process.
Figure 23:
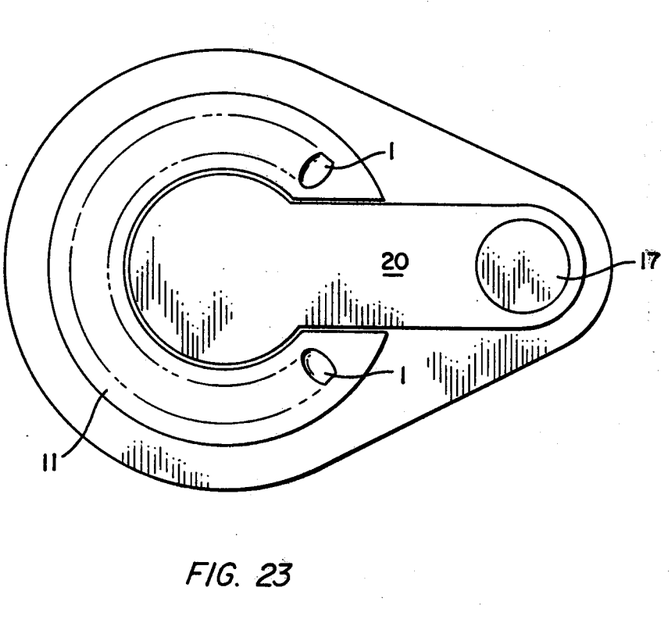
FIG. 23 is a plan view of the apparatus shown in FIG. 22.

A complete automatic system, e.g. for blood group analysis, is shown diagrammatically in FIG. 22. Rising from a base 16 is a column 17 having secured to it for example three arms 18–20 (see also FIG. 23). Column 17 is arranged so that it cannot rotate around its axis in bearing 21 of base 16, nor can the arms 18–20 rotate around column 17. Consequently, the various stations of the apparatus can be arranged in a vertically stepped or staged system around a main vertical axis which is the centrifuging axis Z.

Figure 18:
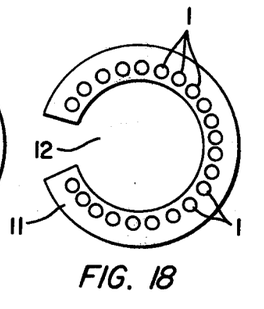

A cylindrical sleeve 22 is secured to the two top arms 19, 20 and guides the supports 11 (e.g. of FIG. 18) and allows the same to slide downwardly. The supports 11 as shown in FIG. 18 and because of the recess in them, can be fitted on the arm 20; they are engaged by a system (not shown) which lowers them stepwise along the axis Z as embodied by the sleeve 22. After the specimen and reagents have been introduced at 23, the mixture has sufficient time for incubation as its travels downwards along sleeve 22.

After passing along the incubation path the vessel-carrying supports 11 are placed automatically by the step-by-step system in a centrifuge 24 which at this time is stationary. The mixture which has been incubated and which is present at location 4 in vessel 1 is hurled during centrifuging along the intermediate zone and the inclined surface or wall 6 as far as the vessel base location 7. Upon the completion of centrifuging the supports 11 move stepwise along a guidesleeve 25 retained by an arm 18 long enough for the mixture of specimen and reagents to separate out into an agglutinated part remaining on the vessel base 7 and an unagglutinated part which descends along the inclined wall 6, so that the nature of the reaction can be defined in accordance with FIGS. 5a–5b or FIGS. 6a–6b.

When a particular support 11 reaches the bottom position, the nature of the reaction can be measured by means of a microscope arrangement 26 (see also FIG. 9) comprising a light source 27, an optical system 32–35 and a photoelectric cell 30 connected to an indicating instrument.

The system for conveying the supports along the equipment is considered to be known and so has been neither described nor shown. Similar considerations apply to the elements for loading and unloading the supports.

We claim:

1. An analysis process based on an agglutination reaction, comprising (a) mixing a specimen for analysis with one or more reagents in a vessel of progressively decreasing cross-section in a first direction leading to a base thereof, (b) incubating the mixture, (c) centrifuging the incubated mixture at least once about an axis outside the vessel so as to hurl the particles in said first direction onto the vessel base, the same being disposed substantially in the direction of the centrifugal force, with the result that the agglutinated particles adhere to the vessel base whereas the unagglutinated elements remain free thereon, (d) ceasing said centrifuging, and (e) determining the nature of the reaction which has occurred by observing the presence or absence of the agglutinated or non-agglutinated elements after a time interval sufficient for their separation along a path downwardly inclined from the vessel base.

2. A process according to claim 1 wherein in regard to the resulting product of operations (a), (b), (c) and (d) said operations (a), (b), (c) and (d) are repeated on said resulting product and a different reagent, and thereafter operation (e) is performed.

3. A process according to claim 1 wherein before said mixing operation (a), the vessel is covered internally with a thin layer of protein.

4. A process according to claim 1 wherein in order to facilitate said mixing operation (a), the vessel has imparted to it, before and/or during said incubation operation (b), a vibratory motion in a horizontal and/or vertical plane.

5. A process according to claim 1 wherein the nature of the reaction is determined automatically by means comprising at least a microscope arrangement and a photoelectric means.

6. A process according to claim 1 wherein in the case of the specimen to be analyzed or the reagent being radioactive or having an added radioactive substance, the nature of the reaction is determined automatically by means comprising a radioactivity counter.

7. A process according to claim 1 wherein in the case of blood analysis the blood specimen is preliminarily separated at least into globules and plasma by centrifuging.

8. A process according to claim 7 wherein the globule specimen to be analyzed is treated with an enzyme accelerating the agglutination reaction.

9. A process according to claim 1 wherein in the case of a complex agglutination reaction, at least one further step is performed to facilitate agglutination.

10. A process according to claim 9 wherein the centrifuged mixture is washed by addition and removal of an appropriate washing liquid, such as a physiological solution.

11. A process according to claim 9 wherein the mixture is returned to the suspended state in the vessel by means of a stream of a physiological solution.

12. A process according to claim 9 wherein the mixture is returned to the suspended state in the vessel by means of a vibratory motion in a horizontal and/or vertical plane.

13. In an apparatus for performing an analysis based on an agglutination reaction, the arrangement comprising a support having at least one vessel associated therewith, said vessel being formed with an aperture for the charging of at least one specimen and at least one reagent and including a first location for the deposition and mixing of said specimen and reagent substances, and means for centrifuging the reaction mixture of said specimen and reagent substances, the form of said at least one vessel being such as to have a progressively decreasing cross-section in the direction away from the centrifuging axis and a surface which inclines outwardly relative to the centrifuging axis, the inclined surface of said vessel extending as far as the region of narrowest cross-section thereof, whereby the form of said at least one vessel is such that the agglutinated particles following centrifuging adhere to said inclined surface whereas the unagglutinated portions remain free for displacement thereon.

14. Apparatus according to claim 13 wherein the inclined surface forms with the horizontal an angle of from 30° to 60°.

15. Apparatus according to claim 13 wherein the inclined surface forms with the horizontal an angle preferably of from 45° to 55°.

16. Apparatus according to claim 13 wherein the terminal part of the vessel is substantially bounded by the inclined surface at the bottom and by a tunnel-shaped arc at the top.

17. Apparatus according to claim 13 wherein each vessel is made of a transparent substance, at least in the region of the inclined surface.

18. Apparatus according to claim 13 wherein a transition zone exists between said first location and the inclined surface and said transition zone is also inclined relative to the horizontal.

19. Apparatus according to claim 18 wherein the inclination angle of the transition zone coincides with the inclination angle of the inclined surface, such that the transition zone merges steplessly into the inclined surface.

20. Apparatus according to claim 18 wherein the inclination angle of the transition zone is a fraction of the inclination angle of the inclined surface.

21. Apparatus according to claim 13 wherein a number of vessels are disposed in an open or closed circle on a support.

22. Apparatus according to claim 21 wherein the support is a closed ring.

23. Apparatus according to claim 21 wherein the support is an open ring.

24. Apparatus according to claim 21 wherein the support is a disc.

25. Apparatus according to claim 24 wherein the disc is formed with a recess or the like which extends from the outside to beyond the center.

26. Apparatus according to claim 21 wherein stations of the various operations of mixing and/or incubating, centrifuging, washing, suspending, measuring etc. are arranged coaxially along a vertical axis.

27. Apparatus according to claim 26 including means for producing a stepwise movement of the vessel supports between consecutive stations.

* * * * *